(12) United States Patent
Hesse et al.

(10) Patent No.: US 6,437,166 B1
(45) Date of Patent: Aug. 20, 2002

(54) METHOD FOR REPROCESSING REACTION MIXTURES CONTAINING DIARYL CARBONATE

(75) Inventors: Carsten Hesse, Tönisvorst; Ursula Jansen, Neuss; Johann Rechner, Kempen; Claus-Peter Reisinger, Krefeld, all of (DE); Rob Eek, Bergen op Zoom (NL); Kaspar Hallenberger, Leverkusen; Martin Friedrich, Köln, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/868,412

(22) PCT Filed: Dec. 9, 1999

(86) PCT No.: PCT/EP99/09695

§ 371 (c)(1),
(2), (4) Date: Jun. 14, 2001

(87) PCT Pub. No.: WO00/37418

PCT Pub. Date: Jun. 29, 2000

(30) Foreign Application Priority Data

Dec. 22, 1998 (DE) .......................... 198 59 296

(51) Int. Cl.[7] .............................................. C07C 69/96
(52) U.S. Cl. ...................................................... 558/274
(58) Field of Search ......................................... 558/274

(56) References Cited

U.S. PATENT DOCUMENTS

| | | | |
|---|---|---|---|
| 5,239,106 A | 8/1993 | Shafer et al. | 558/274 |
| 5,312,955 A | 5/1994 | Pressman et al. | 558/260 |
| 5,498,747 A | 3/1996 | Pohl et al. | 560/25 |

FOREIGN PATENT DOCUMENTS

| | | |
|---|---|---|
| EP | 0 687 666 | 12/1995 |
| EP | 0 801 052 | 10/1997 |

*Primary Examiner*—T. A. Solola
*Assistant Examiner*—Joseph Murray
(74) *Attorney, Agent, or Firm*—Joseph C. Gil; James R. Franks

(57) ABSTRACT

A process for the work up of reaction mixtures containing diaryl carbonate, aromatic hydroxy compound, water, base and quaternary salt, which are obtained in the preparation of diaryl carbonates by direct carbonylation of aromatic hydroxy compounds, is described. In the process of the present invention an adduct of diaryl carbonate and aromatic hydroxy compound is crystallized from the reaction mixture. A distillate comprising aromatic hydroxy compound is removed from the liquid phase either prior to or after crystallization of the adduct of diaryl carbonate and aromatic hydroxy compound. The liquid phase remaining after the crystallization and distillation steps may be recycled, without further work up, back to the direct carbonylation process step by which the diaryl carbonate is initially prepared.

7 Claims, No Drawings

METHOD FOR REPROCESSING REACTION MIXTURES CONTAINING DIARYL CARBONATE

CROSS REFERENCE TO RELATED PATENT APPLICATIONS

The present patent application claims the right of priority under 35 U.S.C. 119 and 35 U.S.C. 365 of International Application No. PCT/EP99/09695, filed Dec. 9, 1999, which was published in German as International Patent Publication No. WO 00/37418, on Jun. 29, 2000.

FIELD OF THE INVENTION

The present invention relates to a process for the work up of reaction mixtures containing diaryl carbonate, aromatic hydroxy compound, water, base and quaternary salt which are obtained in the preparation of diaryl carbonates by direct carbonylation of aromatic hydroxy compounds. In the process according to the invention, an adduct of diaryl carbonate and aromatic hydroxy compound is crystallised from the reaction mixture on the one hand, and a distillate containing the aromatic hydroxy compound is removed from the liquid phase on the other hand. The liquid phase is then recycled to the reaction step of direct carbonylation. Deactivation of the recycled catalyst system is minimised by the process according to the invention.

BACKGROUND OF THE INVENTION

A process for the isolation of adduct crystals of diphenyl carbonate (DPC) and phenol in a molar ratio of 1:1 from phenolic solutions with a DPC content of 20 to 70 wt. % is disclosed in U.S. Pat. No. 5,239,106. During the preparation of diphenyl carbonate, the water formed during the reaction is removed by means of a molecular sieve. In view of the amounts of molecular sieve required and the expensive regeneration of the loaded molecular sieve, conversion of this process to an industrial scale is economically unattractive.

According to the disclosure of EP-A 583 938, the crystallisation mother liquor is recycled to the reaction step in the process described in U.S. Pat. No. 5,239,106. As can be derived from example 1 and 2 of EP-A 583 938, recycling the mother liquor to the reaction leads to considerable deactivation of the catalyst system.

An alternative process for the preparation of diaryl carbonates is derived from U.S. Pat. No. 5,498,742 wherein the water formed in the reaction is stripped by excess reaction gas. If the diaryl carbonate formed is separated by crystallisation and the crystallisation mother liquor recycled to the reaction step, losses of yield and selectivity are observed in this case, too.

SUMMARY OF THE INVENTION

It has now been found that the deactivation of the catalyst system can be avoided to a large extent if a part of the aromatic hydroxy compound is removed by distillation before solutions containing catalyst are recycled to the reaction step.

The invention provides a process for the work up of reaction mixtures from the preparation of diaryl carbonates by direct carbonylation of aromatic hydroxy compounds, wherein an adduct of diaryl carbonate and aromatic hydroxy compound is crystallised from a reaction mixture containing diaryl carbonate, aromatic hydroxy compound, water, base and quaternary salt, at least 0.2 wt. %, based on the reaction mixture prior to crystallisation, of a distillate containing the aromatic hydroxy compound is removed from the liquid phase at pressures from 10 to 200 mbar and at temperatures from 40 to 160° C., and the liquid phase is then recycled to the reaction step.

DETAILED DESCRIPTION OF THE INVENTION

The crystallisation of the diphenyl carbonate adduct may take place in principle before or after the removal of the distillate containing the aromatic hydroxy compound. In the first case mentioned, it is important to ensure that the amount of aromatic hydroxy compound removed from the reaction mixture is not high enough for the diaryl carbonate content in the liquid phase to rise above 70 wt. % otherwise the diaryl carbonate adduct will no longer crystallise out, only pure diaryl carbonate. In preference, the amount of distillate removed will be such that 25 to 65 wt. %, particularly preferably 35 to 55 wt. % of diaryl carbonate is contained in the reaction mixture prior to crystallisation in order to provide a particularly effective crystallisation.

In order to minimise deactivation of the catalyst system, at least 0.2 wt. % of the reaction mixture must be removed as distillate after the reaction before the liquid phase can be recycled to the reaction step. If it is not necessary to enrich the reaction mixture with diaryl carbonate prior to work up, it is generally sufficient to remove an amount of distillate corresponding to 0.2 to 5 wt. % of the reaction mixture. If distillation is carried out after the crystallisation step, it is also preferable to remove only an amount of distillate corresponding to 0.2 to 5 wt. % of the reaction mixture in order to expose the catalyst components contained in the liquid phase to the least possible thermal stress and to keep the amount of energy required low.

The preparation of diaryl carbonates by direct carbonylation of aromatic hydroxy compounds is well known (see, for example, U.S. Pat. No. 4,349,485, U.S. Pat. No. 5,231, 210, EP-A 667 336, EP-A 858 991, U.S. Pat. No. 5,760,272).

An aromatic hydroxy compound corresponding to the formula

R—O—H (I), wherein
R means substituted or unsubstituted $C_6$–$C_{12}$-aryl, preferably substituted or unsubstituted phenyl, particularly preferably unsubstituted phenyl,
is reacted with carbon monoxide and oxygen in the presence of a platinum metal catalyst, a cocatalyst, a quaternary salt and a base at a temperature from 30 to 200° C., preferably 30 to 150° C., particularly preferably 40 to 120° C. and at a pressure from 1 to 200 bar, preferably 2 to 100 bar, particularly preferably 5 to 50 bar.

The composition of the reaction gases carbon monoxide and oxygen may be varied within wide concentration limits, but a $CO:O_2$ molar ratio (standardised to CO) of 1:(0.001–1.0), preferably 1:(0.01–0.5) and particularly preferably 1:(0.02–0.3) is advantageously obtained. The oxygen partial pressure at these molar ratios is high enough for high space-time yields to be obtained and at the same time to prevent the formation of explosive mixtures of carbon monoxide/oxygen gas. The reaction gases are not subject to any particular purity requirements. So synthesis gas may be used as a source of CO and air as a source of $O_2$, but it is important to ensure that no catalyst poisons such as, e.g.

sulfur or compounds thereof are introduced. Pure CO and pure oxygen are used in preference.

The aromatic hydroxy compounds capable of reaction are, for example, phenol, o-, m- or p-cresol, o-, m- or p-chlorophenol, o-, m- or p-ethylphenol, o-, m- or p-propylphenol, o-, m- or p-methoxyphenol, 2,6-dimethylphenol, 2,4-dimethylphenol, 3,4-dimethylphenol, 1-naphthol, 2-naphthol and bisphenol A, preferably phenol. Generally speaking, in the event of the aromatic hydroxy compound being substituted, 1 or 2 substituents are present, these being $C_1$–$C_4$-alkyl, $C_1$–$C_4$-alkoxy, fluorine, chlorine or bromine.

Suitable bases are alkali, quaternary ammonium or quaternary phosphonium salts of aromatic hydroxy compounds corresponding to formula (I). Alternatively, trialkylamines such as tributylamine, diisopropylethylamine, DBU, DBN or other bases e.g. potassium-tert.-butanolate may be used.

The base is added in an amount independent of the stoichiometry. The ratio of platinum metal, e.g. palladium to base is chosen preferably such that, per gram atom of platinum metal, e.g. palladium, 0.1 to 500, preferably 0.3 to 200 and particularly preferably 0.9 to 130 equivalents of base are used.

The process is carried out preferably without solvent. Of course, inert solvents may also be used. Examples of solvents include dimethylacetamide, N-methylpyrrolidone, t-butanol, cumyl alcohol, isoamyl alcohol, tetramethylurea, diethylene glycol, halogenated hydrocarbons (e.g. chlorobenzene or dichlorobenzene) and ethers, such as dioxane, tetrahydrofuran, t-butylmethylether and etherified glycols.

Suitable platinum metal catalysts are composed of at least one noble metal of group VIII, preferably palladium. It may be added in various forms. Palladium may be used in the metallic form or preferably in the form of palladium compounds in oxidation states 0 and +2, such as, for example, palladium (II) acetylacetonate, halides, carboxylates of $C_2$–$C_6$-carboxylic acids, nitrate, oxides or palladium complexes which may contain, for example, olefins, amines, phosphines and halides. Palladium bromide and palladium acetylacetonate are particularly preferred. The amount of platinum metal catalyst is not restricted. The amount of catalyst added is usually such that the concentration of the metal in the reaction batch is 1–3000 ppm, concentrations from 5–500 ppm being preferred.

The cocatalyst used is a metal of groups III A, III B, IV A, IV B, V B, I B, II B, VI B, VII B, the rare earth metals (atomic numbers 58–71) or of the iron group of the periodic system of elements (Mendeleev), whereby the metal may be used in various oxidation states. Mn, Cu, Co, V, Zn, Ce and Mo are used in preference, e.g. manganese (II), manganese (III), copper (I), copper (II), cobalt (II), cobalt (III), vanadium (III) and vanadium (IV). The metals may be used, for example, as halides, oxides, carboxylates of $C_2$–$C_6$-carboxylic acids, diketonates or nitrates and as complex compounds containing, for example, carbon monoxide, olefins, amines, phosphines and halides. Mn, Cu, Mo and Ce are used in particular preference. Manganese compounds are used more particularly preferably in the process according to the invention, particularly preferably manganese (II) complexes, and more particularly preferably manganese (II) acetylacetonate or manganese (III) acetylacetonate.

The cocatalyst is added in an amount such that its concentration is from 0.0001 to 20 wt. % of the reaction mixture; the concentration range is preferably 0.005 to 5 wt. % and particularly preferably 0.01 to 2 wt. %.

The quaternary salts may be, for example, ammonium, guanidinium, phosphonium or sulfonium salts substituted with organic radicals. Ammonium, guanidinium, phosphonium and sulfonium salts bearing $C_6$ to $C_{10}$-aryl, $C_7$ to $C_{12}$-aralkyl and/or $C_1$ to $C_{20}$-alkyl radicals as organic radicals and a halide, tetrafluoroborate or hexafluorophosphate as anion are suitable. Ammonium salts bearing $C_6$ to $C_{10}$-aryl, $C_7$ to $C_{12}$-aralkyl and/or $C_1$ to $C_{20}$-alkyl radicals as organic radicals and a halide as anion are used in preference, tetrabutylammonium bromide being particularly preferred. The amount of such a quaternary salt may be, for example, 0.1–20 wt. %, based on the weight of the reaction mixture. This amount is preferably 0.5–15 wt. %, particularly preferably 1–5 wt. %.

Homogenous catalyst systems may be used for the preparation of diaryl carbonate, or heterogeneous catalysts in which the platinum metal or the platinum metal and the cocatalyst are deposited on a heterogeneous support. In the case of heterogeneous catalyst systems, the other components of the catalyst system such as the base, the quaternary compound and optionally the cocatalyst are, moreover, dissolved homogeneously in the reaction solution.

The heterogeneous supported catalyst may be used in a fixed manner in agitated vessels, bubble columns, a trickle phase reactor or cascades of said reactors. Separation of the supported catalyst from the reaction mixture is then completely unnecessary.

A reaction mixture containing diaryl carbonate, aromatic hydroxy compound, water, base and quaternary salt is obtained in the preparation of diaryl carbonates by direct carbonylation of aromatic hydroxy compounds. If a homogeneous catalyst system is used, the reaction mixture also contains platinum metal catalyst and cocatalyst.

The removal of the distillate containing the aromatic hydroxy compound from the reaction mixture is carried out at pressures from 10 to 200 mbar and at temperatures from 40 to 160° C., preferably 50 to 120° C., particularly preferably 60 to 100° C.

Crystallisation of the liquid phase may take place by various crystallisation methods familiar to the expert, for example, fractional melt crystallisation, layer crystallisation or static or dynamic suspension crystallisation. Crystallisation of the liquid phase takes place preferably by suspension crystallisation.

After crystallisation and removal of the distillate, the liquid phase, optionally after separation of deactivated catalyst constituents by filtration, is recycled without further work up to the reaction step of direct carbonylation.

After separation from the mother liquor, the diaryl carbonate adduct crystals are preferably washed to remove adhering impurities, for example, catalyst residues. Washing may be carried out, for example, with water or aromatic hydroxy compound. The crystals are, however, washed preferably with a solution of diaryl carbonate in aromatic hydroxy compound since losses of yield are thereby minimised. The diaryl carbonate concentration of the wash solution is preferably 10 to 25 wt. %.

The wash solution may then be fed to the reaction mixture obtained in the reaction step of direct carbonylation. The diaryl carbonate contained in the wash solution can thereby be recovered.

EXAMPLES

Example 1

Comparison Example 1200 g per hour of a reaction solution composed of about 120 ppm Pd (as PbBr$_2$), about 300 ppm Mn (as Mn(acac)$_2$), about 2.5 wt. % of TBAB (tetrabutylammonium bromide), about 1.5 wt. % of TBAP (tetrabutylammonium phenolate), 20 wt. % of diphenylcarbonate and phenol were metered into an autoclave at about 85° C. and 14 bar by means of two metering pumps. The liquid level in the reactor was set at about 1200 ml. At the same time, about 700 NL/h of a gas mixture composed of 2.5 vol. % of oxygen, 1.5 vol. % of inert gas ($N_2$, Ar et.) and the remainder to 100% carbon monoxide were metered into the autoclave.

The liquid stream from the reactor was removed continuously and fed to a tubular crystalliser; a quasi-continuous method of operation could be obtained by the timed use of several crystallisers. The DPC content of the reaction mixture was about 30 wt. %. The seeding temperature and the crystallisation temperature were 39° C., the final cooling temperature was 20° C., the rate of cooling was 3 K/h. After the mother liquor had been drained off, the crystalline product was purified by partial melting. After filtration, the mother liquor and condensation solution were recycled together to the reactor without further work up by means of the third metering pump.

At the same time, the throughputs of the first two metering pumps and the concentrations of the catalyst components were adjusted such that the concentrations and mass flows of the reactor feed corresponded to the values given above. The catalyst supplements corresponded to the amounts filtered off. As the operation proceeded, mother liquor and condensation solution were recycled constantly to the reaction as described above. The amounts of DPC and PhOH removed were recycled to the system in the form of fresh phenol, distributed between the first two metering pumps.

The distribution between crystalline product and sum of the recycle solutions was about 1:5.3. The crystalline product was composed of 62 wt. % DPC, 37.5 wt. % phenol and contained traces of catalyst components and by-products.

Even after the first recycle, the space-time yield of the reaction fell from about 98 g/lh DPC to 33 g/lh. Initially, no crystalline product could be obtained in the crystallisers. After an equilibrium had been obtained in the apparatus, it was possible to obtain small amounts of crystalline product corresponding to the space-time yield.

Example 2

Example 1 was repeated except that the combined recycle solution, i.e. mother liquor and condensation solution, after filtration, underwent a purification step by distillation in a thin-film evaporator at 70° C. and 60 mbar. About 40 g/h (3.3 wt. %) of phenol and low-boiling products were separated from the mother liquor in this distillation and the recycle solution was then fed to the reaction as described in example 1.

Until an equilibrium had been obtained in the apparatus, the space-time yield fell from about 96 g/lh to 81 g/lh. The amount of DPC corresponding to the space-time yield could be removed continuously in the crystallisers in the form of DPC/PhOH crystalline product.

Example 3

Example 1 was repeated except that the DPC content in the reactor feed was about 10 wt. %. After the reaction the DPC content was about 20 wt. % and the space-time yield of DPC was about 99 g/lh. Before the reaction solution reached the crystallisers, low-boiling products and phenol were removed therefrom at 100° C. and about 20 mbar by means of a thin-film evaporator so that the DPC content rose to about 33 wt. %. To this end, about one third of the original solution had to be removed by distillation.

The subsequent crystallisation took place as described in example 1. The distribution between crystalline product and sum of the recycle solutions was about 1:5.4. The crystalline product was composed of 61 wt. % of DPC, 38.5 wt. % of phenol and contained traces of catalyst components and by-products. The recycling of the combined mother liquors and condensation solutions and the metering of the catalyst supplement by means of metering pumps 1 and 2 took place as described in example 1.

After an equilibrium had been obtained in the apparatus, the space-time yield was still about 79 g/lh. The amount of DPC corresponding to the space-time yield could be removed continuously in the crystallisers in the form of DPC/PhOH crystalline product.

What is claimed is:

1. A process comprising the steps of:
   (a) preparing a diaryl carbonate by means of a direct carbonylation reaction, said direct carbonylation reaction resulting in the formation of a first mixture comprising said diaryl carbonate, an aromatic hydroxy compound, water, base and quaternary salt;
   (b) removing at least 0.2 wt. %, based on the weight of said first mixture, of a distillate comprising said aromatic hydroxy compound, from the liquid phase of said first mixture, at pressures from 10 to 200 mbar and at temperatures of from 40 to 160° C., the removal to said distillate resulting in the formation of a second mixture;
   (c) crystallizing an adduct of said diaryl carbonate and said aromatic hydroxy compound from said second mixture;
   (d) separating said crystallized adduct from said second mixture, the separation of said crystallized adduct resulting in the formation of a third mixture; and
   (e) recycling said third mixture, without further work up, to said direct carbonylation reaction of step (a).

2. The process of claim 1, wherein said direct carbonylation reaction of step (a) comprises reacting said aromatic hydroxy compound with carbon monoxide and oxygen in the presence of a platinum metal catalyst, a cocatalyst, said quaternary salt and said base at a temperature from 30 to 200° C., and at a pressure of from 1 to 200 bar.

3. The process of claim 2 wherein in step (e) deactivated platinum metal catalyst and cocatalyst are separated from said third mixture prior to recycling the liquid phase of said third mixture to the direct carbonylation reaction of step (a).

4. A process comprising the steps of:
   (a) preparing a diaryl carbonate by means of a direct carbonylation reaction, said direct carbonylation reaction resulting in the formation of a first mixture comprising said diaryl carbonate, an aromatic hydroxy compound, water, base and quaternary salt;
   (b) crystallizing an adduct of said diaryl carbonate and said aromatic hydroxy compound from said first mixture;
   (c) separating said crystallized adduct from said first mixture, the separation of said crystallized adduct resulting in the formation of a second mixture;
   (d) removing 0.2 to 5 wt. %, based on the weight of said second mixture, of a distillate comprising said aromatic hydroxy compound, from the liquid phase of said second mixture, at pressures from 10 to 200 mbar and at temperatures of from 40 to 160° C., the removal to said distillate resulting in the formation of a third mixture; and
   (e) recycling said third mixture, without further work up, to said direct carbonylation reaction of step (a).

5. The process of claim 4, wherein said direct carbonylation reaction of step (a) comprises reacting said aromatic hydroxy compound with carbon monoxide and oxygen in the presence of a platinum metal catalyst, a cocatalyst, said quaternary salt and said base at a temperature from 30 to 200° C., and at a pressure of from 1 to 200 bar.

6. The process of claim 5 wherein in step (e) deactivated platinum metal catalyst and cocatalyst are separated from said third mixture prior to recycling the liquid phase of said third mixture to the direct carbonylation reaction of step (a).

7. The process of claim 1, wherein distillate is removed from said first mixture in step (b) in a quantity such that the diaryl carbonate content of said second mixture is 25 to 65 wt. %, based on the weight of said second mixture.

* * * * *